US009080953B2

(12) United States Patent
Heidrich et al.

(10) Patent No.: US 9,080,953 B2
(45) Date of Patent: Jul. 14, 2015

(54) OPTICAL RESONATOR FOR SENSOR ARRANGEMENT AND MEASURING METHOD

(71) Applicant: Fraunhofer-Gesellschaft zur Foerderung der angewandten Forschung e.V., Munich (DE)

(72) Inventors: Helmut Heidrich, Berlin (DE); Peter Lützow, Berlin (DE); Daniel Pergande, Berlin (DE); Alethea Vanessa Gomez Zamora, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 14/350,804

(22) PCT Filed: Oct. 4, 2012

(86) PCT No.: PCT/EP2012/004219
§ 371 (c)(1),
(2) Date: Apr. 9, 2014

(87) PCT Pub. No.: WO2013/053459
PCT Pub. Date: Apr. 18, 2013

(65) Prior Publication Data
US 2014/0253917 A1    Sep. 11, 2014

(30) Foreign Application Priority Data
Oct. 10, 2011   (EP) .................................. 11075224

(51) Int. Cl.
*G01N 21/27*   (2006.01)
*G01N 21/39*   (2006.01)
(Continued)

(52) U.S. Cl.
CPC ............... *G01N 21/27* (2013.01); *G01J 3/0205* (2013.01); *G01J 3/0256* (2013.01); *G01J 3/10* (2013.01);
(Continued)

(58) Field of Classification Search
CPC ..... G01J 3/26; G01N 21/7746; G01N 21/255; G02B 6/29343
See application file for complete search history.

(56) References Cited

U.S. PATENT DOCUMENTS 6,721,053 B1 * 4/2004 Maseeh ........................ 356/436
7,796,262 B1   9/2010 Wang et al.
(Continued)

FOREIGN PATENT DOCUMENTS

EP        2267432 A1      12/2010
WO    WO02093221 A2      11/2002
WO    WO2011000494 A1    1/2011

OTHER PUBLICATIONS

Braun, Ralf-Peter et al., "Optical Microwave Generation and transmission Experiments in the 12- and 60- GHz Region for Wireless Communications", IEEE Transactions on Microwave Theory and Techniques, vol. 46, No. 4, Apr. 1998, pp. 320-330.
(Continued)

*Primary Examiner* — Kara E Geisel
(74) *Attorney, Agent, or Firm* — Faegre Baker Daniels LLP

(57) ABSTRACT

A sensor arrangement including a light source, a first optical element, a second optical element, a first photo detector, and a second photo detector. The light source is optically coupled to the first optical element that is optically coupled to the second optical element. The first photo detector is optically coupled to the first optical element for detecting a first component of the part of the light which is not transmitted by the second optical element, and the second photo detector is optically coupled to the second optical element for detecting a second component of the part of the light which is transmitted by the second optical element. One of the first and the second optical elements is an optical filter and the other is a sensor element, where the sensor element or the filter is tunable.

14 Claims, 4 Drawing Sheets

(51) Int. Cl.

| | |
|---|---|
| *G01N 21/77* | (2006.01) |
| *G01J 3/02* | (2006.01) |
| *G01J 3/10* | (2006.01) |
| *G01J 3/26* | (2006.01) |
| *G01N 21/25* | (2006.01) |
| *G01N 21/23* | (2006.01) |
| *G01N 21/81* | (2006.01) |
| *G02B 6/12* | (2006.01) |
| *G02B 6/293* | (2006.01) |

(52) U.S. Cl.
CPC ............... *G01J 3/26* (2013.01); *G01N 21/255* (2013.01); *G01N 21/39* (2013.01); *G01N 21/7746* (2013.01); *G01N 21/23* (2013.01); *G01N 21/81* (2013.01); *G01N 2021/7776* (2013.01); *G02B 6/12007* (2013.01); *G02B 6/29343* (2013.01)

(56) References Cited

U.S. PATENT DOCUMENTS

| | | |
|---|---|---|
| 7,903,906 B2 | 3/2011 | Smith et al. |
| 2004/0023396 A1 | 2/2004 | Boyd et al. |
| 2004/0146431 A1 | 7/2004 | Scherer et al. |
| 2004/0190148 A1* | 9/2004 | Clark et al. ............... 359/629 |
| 2005/0035278 A1 | 2/2005 | Margalit et al. |
| 2006/0198415 A1* | 9/2006 | Yamazaki .................. 372/94 |
| 2006/0227331 A1 | 10/2006 | Vollmer et al. |
| 2010/0086261 A1 | 4/2010 | Tanaka |
| 2014/0326858 A1 | 11/2014 | Heidrich et al. |

OTHER PUBLICATIONS

Eisenhart, Robert L., "A Novel Wideband TM01-to-TE11 Mode Convertor", copyright 1998, IEEE, pp. 249-252.

Braun, Ralf-Peter et al., "Optical Microwave Generation and transmission Experiments in the 12- and 60- GHz Region for Wireless Communications", IEEE Transactions on Microwave Theory and Techniques, vol. 46, No. 4, Apr. 1998, pp. 320-330

International Preliminary Report on Patentability, issued in PCT/EP2012/004219, completed Jan. 14, 2014, 16 pages.

Claes, Tom et al., "Vernier-cascade label-free biosensor with integrated arrayed waveguide grating for wavelength interrogation with low-cost broadband source", Optics Letters, vol. 36, No. 17, Sep. 1, 2011, pp. 3320-3322.

European Search Report issued in EP Application No. 11075212, dated Jan. 27, 2012, 11 pages.

European Search Report issued in EP Application No. 11075224, dated Mar. 15, 2012, 7 pages.

International Preliminary Report on Patentability, Chapter II, issued in PCT/EP2012/002737, completed Nov. 15, 2013, 24 pages.

International Search Report and Written Opinion issued in PCT/EP2012/002737, mailed Sep. 17, 2012, 13 pages.

International Search Report and Written Opinion issued in PCT/EP2012/004219, mailed Nov. 29, 2012, 10 pages.

Jin, Lei et al., "Optical Waveguide Double-Ring Sensor Using Intensity Interrogation With a Low-Cost Broadband Source", Optics Letters, vol. 36, No. 7, Apr. 1, 2011, pp. 1128-1130.

Lutzow, Peter et al., "Integrated Optical Sensor Platform for Multiparameter Bio-Chemical Analysis", Optics Express, vol. 19, No. 14, Jul. 4, 2011, pp. 13277-13284.

Mesaritakis, Charis et al., "Adaptive Interrogation for Fast Optical Sensing Based on Cascaded Micro-Ring Resonators", IEEE Sensors Journal, vol. 11, No. 7, Jul. 1, 2011, pp. 1595-1601.

Tamee, Kreangsak et al., "Distributed Sensors Using a PANDA Ring Resonator type in Multiwavelenth Router", IEEE Sensors Journal, vol. 11, No. 9, Sep. 9, 2011, pp. 1987-1992.

* cited by examiner

OPTICAL RESONATOR FOR SENSOR ARRANGEMENT AND MEASURING METHOD

CROSS-REFERENCE TO RELATED APPLICATION

This application is a national phase application of PCT Application No. PCT/EP2012/004219, internationally filed Oct. 4, 2012, which claims priority to European Application No. 11 075 224.3, filed Oct. 10, 2011, both of which are herein incorporated by reference in their entirety.

TECHNICAL FIELD

The disclosure relates to an optical sensor arrangement for measuring an observable.

BACKGROUND

Optical resonators have been used as sensor elements by exposing the respective resonator to an observable and by detecting shifts of resonance wavelengths caused by the observable.

In this context, optical micro ring resonators have a great importance due to their high quality as optical sensors. A sensor of this type is very sensitive as a surface of the micro ring is scanned by an evanescent field of a light wave propagating within the micro ring. Currently, micro ring resonators are used to perform measurements with a selectively working absorber surface, which plays an important role for an adequate specificity of the sensor. Molecules adsorbed or collected at the surface cause an optical ring circumference to vary. Thus, an effective refractive index of the micro ring resonator changes such that wavelengths of resonant modes are shifted. The goal is to reliably measure changes in the refractive index of the surrounding medium even if their relative size is far less than $10^{-5}$. Similarly, micro ring resonators can also be used for measuring temperature effects (this is possible if resonance shifts are caused by a temperature dependence of the refractive index), mechanical influences (e.g. via stress birefringence) or humidity (as water will condensate on a surface of the micro ring and lead to a change in the effective refractive index).

In order to achieve sufficiently high resolutions, known sensors of this type will need a tuneable diode laser. This is due to the fact that a wavelength resolution of the sensor arrangement is directly related to the sensor sensitivity. Problems may be caused by the fact that tuneable diode lasers are very expensive.

SUMMARY

It is an object of the disclosure to describe a comparable optical sensor arrangement and to suggest a method for measuring an observable which can be realized at lower costs.

The disclosure relates to an optical sensor arrangement for measuring an observable by means of an optical resonator which is used as a sensor element, an optical length of this resonator being variable depending on the observable. Furthermore, the disclosure relates to a method for measuring an observable which can be performed by a sensor arrangement of this type.

In some embodiments, the optical sensor arrangement for measuring an observable comprises a light source for emitting light of a spectrum containing a plurality of different wavelengths, a first optical element, a second optical element, a first photo detector and a second photo detector. One of the first and the second optical elements is an optical filter for filtering out a subset of said wavelengths, a transmittance of the filter showing at least one peak, the peak coinciding with one of said wavelengths. The remaining of the first and the second optical elements is a sensor element, the sensor element being an optical resonator, an optical length of this resonator being variable depending on the observable. This implies that a resonance wavelength or resonance wavelengths are shifted depending on a magnitude of the observable. In some embodiments, at least one of the sensor element and the filter is tunable. The tunable optical element may, e.g., be tuned by temperature control or by exposing it to an electric field or current. The light source is optically coupled to the first optical element for feeding the light into the first optical element, the first optical element being optically coupled to the second optical element for feeding a part of the light transmitted by the first optical element into the second optical element. The first photo detector is optically coupled to the first optical element for detecting a first component of said part of the light which is not transmitted by the second optical element, the second photo detector being optically coupled to the second optical element for detecting a second component of said part of the light which is transmitted by the second optical element.

This sensor arrangement can be used for accurately measuring the observable by tuning the sensor element or the optical filter, dependent on output signals of the photo detectors, such that a resonance wavelength of the optical resonator or said peak is shifted until the resonance wavelength and the peak are made to coincide. A strength of a control signal applied to the sensor element or to the optical filter for shifting the resonance wavelength or the peak, respectively, in this way when the sensor element is exposed to the observable can be regarded as a measure for the observable.

In some embodiments, a method for measuring an observable, which can be performed using the optical sensor arrangement herein described, comprises
  producing light by means of a light source, the light having a spectrum containing a plurality of different wavelengths,
  feeding the light into a first optical element,
  feeding a part of the light transmitted by the first optical element into a second optical element,
  detecting, by means of at least two photo detectors, a first component and a second component of said part of the light, wherein the first component is not transmitted by the second optical element while the second component is transmitted by the second optical element,
  wherein one of the first and the second optical elements is an optical filter for filtering out a subset of said wavelengths, a transmittance of the filter showing at least one peak, the peak coinciding with one of said wavelengths,
  and wherein the remaining of the first and the second optical elements is a sensor element, the sensor element being an optical resonator, an optical length of this resonator being variable depending on the observable.

In some embodiments, the method further comprises:
  tuning the sensor element or the optical filter by applying, dependent on output signals of the photo detectors, a control signal to the sensor element or to the optical filter such that a resonance wavelength of the optical resonator or said peak is shifted until the resonance wavelength and the peak are made to coincide, a strength of the shifting control signal being a measure for the observable.

In some embodiments, a reference can be obtained by tuning the sensor element or the filter at known external conditions, e.g., before exposing the sensor element to an influence of the observable to be measured, such that the resonance wavelength and the peak coincide. By subsequently exposing the sensor element to the observable and tuning the sensor element or the filter as described above, a shift of the resonance wavelength caused by the observable is compensated. This is why the strength of the control signal can be regarded as a measure for the observable. In the same way, a reference measurement could be performed afterwards, i.e. after the actual measurement which is performed when the sensor element is exposed to the influence of the observable to be detected.

In some embodiments, a high resolution can be obtained, more or less independent from a spectral quality of the light source, due to the fact that the transmittance of the filter shows said peak which is made to coincide with the resonance wavelength by adequately tuning the sensor element or the filter. The light source may, thus, be chosen to be a rather cheap light source like, e.g., a Fabry-Perot laser or an LED. The transmittance of the optical filter may, of course, show additional peaks. The peak which is made to coincide with the resonance wavelength, is a local maximum of the transmittance and the transmittance shows a steep decrease to both sides of the local maximum, the transmittance preferably decreasing to at least almost zero within a small interval surrounding the local maximum. This is how the term "peak" is to be understood in this context.

In some embodiments, the control signal applied for tuning the sensor element or the optical filter can be chosen such that, depending on the exact design of the sensor arrangement, an intensity of the second component or of the first component has a maximum value and/or an intensity of the first component or of the second component has a minimum value, the maximum value and/or the minimum value indicating that said resonance wavelength of the optical resonator and the peak coincide.

In some embodiments, the sensor arrangement comprises a control unit configured for tuning the sensor element or the filter by means of a control signal, the control signal being adapted for shifting, dependent on output signals of the first and the second photodetectors, a resonance wavelength of the optical resonator or said peak such that the resonance wavelength and the peak are made to coincide, a strength of the shifting control signal being a measure for the observable. In this case, the method for measuring the observable can particularly easy be performed using the sensor arrangement.

In some embodiments, the optical filter can be designed as a further optical resonator. Alternatively, the optical filter can be a wavelength selective element comprising an optical grating, e.g. an Arrayed-Waveguide Grating (AWG). Both types of filters are suited for obtaining the desired transmittance showing the at least one peak.

In some embodiments, the sensor element can be realized as a ring resonators, in particular as on optical micro ring resonator, or as a Fabry-Perot resonator. The same applies to the optical filter, which, in some embodiments, is designed as an optical ring resonator or a Fabry-Perot resonator. Using resonators of this kind results in a high resolution as well as in advantageously small dimensions of the sensor arrangement. They can be realized by circular shaped waveguides arranged on a substrate.

In some embodiments, the measured observable which influences the optical length of the sensor element can be at least one of a temperature, a pressure, a mechanical stress, a humidity and a presence or concentration of a substance or of a group of substances to be detected. For realizing a sensitivity for a presence or concentration of a particular substance or group of substances, the sensor element can be covered at least partially with an active layer of a covering material for selectively adsorbing the substance or the group of substances to be detected. For measuring the observable which, in this case, is the presence or the concentration of the particular substance or group of substances, the sensor element can be brought into contact with a fluid to be analysed, an active surface of the sensor element being configured such that the optical length of the sensor element changes when the fluid contains the substance or any of the substances to be detected.

In some embodiments, the sensor arrangement will be compact and robust if it comprises a substrate, the substrate carrying the filter and the sensor element, at least one waveguide being arranged on the substrate for optically coupling the light source, the filter, the sensor element and the photo detectors. Also, the photo detectors and/or the light source may be arranged on the same substrate as well. The substrate can be, for example, a semiconductor chip.

In some embodiments, the light source is tunable, for example by temperature control. The sensor arrangement may, in this case, comprise a feedback control system for controlling the light source dependent on an output signal of the first or the second or a third photo detector, the feedback control system being configured for tuning the light source such that said peak is made to coincide with a maximum of the spectrum of the light emitted by the light source. This can be advantageous in order to make sure that a power of the part of the light fed into the second optical element is sufficiently high for all possible environmental conditions. By means of the feedback control system, the light source can even if the peak of the transmittance shifts due to changing external conditions, be tuned such that said peak is made to coincide with a maximum of the spectrum of the light emitted by the light source. To this end, an output signal of one of the two photo detectors or of a third photo detector can be used as a controlled variable of the feedback control system.

BRIEF DESCRIPTION OF THE DRAWINGS

Embodiments of the disclosure are explained hereafter with reference to FIGS. 1 to 6.

DETAILED DESCRIPTION

Figure 1:
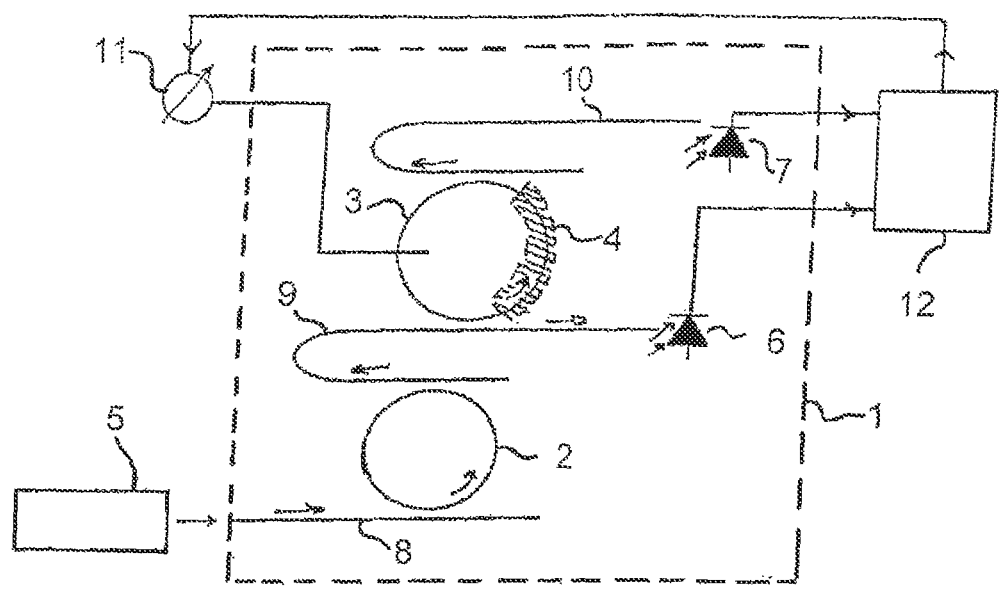
FIG. 1 is a diagram illustrating a schematic top view of an optical sensor arrangement for measuring an observable, according to some embodiments described in the disclosure.

The sensor arrangement shown in FIG. 1 is based on a substrate 1, which is a chip of a semiconductor material and made of a part of a wafer. The substrate 1 carries a first optical element 2 and a second optical element 3. The first optical element 2 is an optical filter and the second optical element 3 is an optical sensor element. In some embodiments, both optical elements 2 and 3 are realized as optical micro ring resonators having, in each case, a circular shaped waveguide core.

An optical length of the second optical element is variable depending on an observable to be measured. The optical length can be expressed as n×2πr where n is an effective refraction index and r is a radius of the respective micro ring. The effective refraction index n depends on a value of the observable as soon as the sensor element is exposed to an influence of this observable. The observable may be, e.g., a temperature, a pressure or any other kind of mechanical stress, a humidity or a presence or concentration of a particular substance or of a group of substances. If the observable to be measured is the presence or the concentration of a particular substance or group of substances, the sensor element is covered at least partially with an active layer 4 of a covering material for selectively adsorbing or collecting molecules of said substance or group of substances.

The sensor arrangement further comprises a light source 5 for emitting light of a spectrum containing a plurality of different wavelengths, a first photo detector 6 and a second photo detector 7. The photo detectors 6 and 7 are, in some embodiments, photo diodes arranged on the substrate 1. The light source 5 may be, for example, an LED or a Fabry-Perot laser source.

By means of a first waveguide 8 arranged on the substrate 1, the light source 5 is optically coupled to the first optical element 2 for feeding the light into the first optical element 2. The first optical element 2 is optically coupled to the second optical element 3 and to the first photo detector 6 by means of a second waveguide 9 for feeding a part of the light transmitted by the first optical element into the second optical element 3, the first photo detector 6 detecting a first component of said part of the light which is not transmitted by the second optical element 3. The second photo detector 7 is coupled, by means of a third waveguide 10, to the second optical element 3 for detecting a second component of said part of the light which is transmitted by the second optical element 3. The second and the third waveguides 9 and 10 are, in the same way as the first waveguide 8, realized by optical wires or waveguide cores which are deposited above the substrate 1 and separated from the substrate 1 by a buffer layer.

Acting as optical filter, the first optical element filters out a subset of the wavelengths emitted by the light source 5. A transmittance of this optical filter shows at least one peak which coincides with one of these wavelengths.

In some embodiments, the sensor element, i.e. the second optical element 3, is tunable. This means that its optical length can be varied—and, thus, resonance wavelengths of the micro ring resonator forming the sensor element be shifted—by means of a tuning device 11. A control unit 12 of the sensor arrangement is configured for tuning the sensor element by means of a control signal, the control signal being adapted for shifting, dependent on output signals of the first photo detector 6 and the second photo detector 7, a resonance wavelength of the sensor element such that the resonance wavelength and said peak are made to coincide. A strength of the shifting control signal can be regarded as a measure for the observable. The control signal can be, e.g., an electrical current or a voltage supplied to the optical element 3.

It should be noted that the different roles of the first optical element 2 and the second optical element 3 may be exchanged in different ways without changing the quality of the arrangement as an optical sensor for measuring the observable. First of all, it is possible that the optical filter is tunable instead of the sensor element and that said peak and said resonance wavelength are made to coincide by tuning the optical filter instead of the sensor element and, thus, by shifting said peak of the transmittance of the filter instead of the resonance wavelength of the sensor element. Furthermore and independent of whether the first optical element 2 or the second optical element 3 is tunable, it is possible to design the first optical element 2 as a sensor element having its optical length influenced by the observable. In this case, the second optical element 3 is chosen to be the optical filter for filtering out a subset of the wavelengths emitted by the light source 5, this filter having a transmittance showing at least one peak which coincides with one of said wavelengths. The optical filter may also be regarded as a spectrometer.

Figure 2:
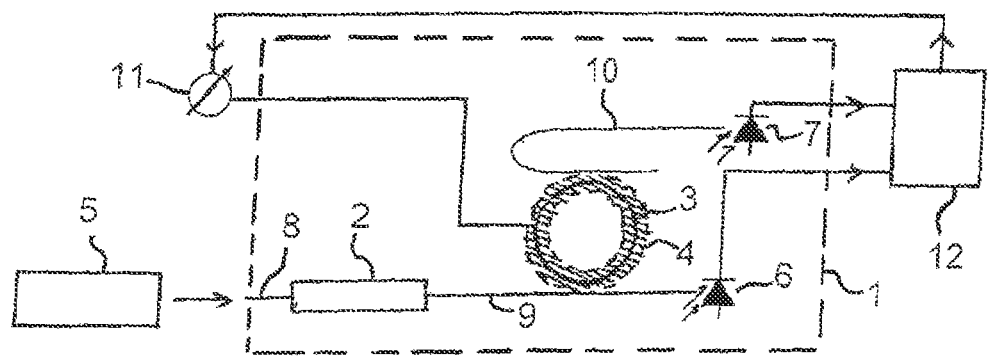
FIG. 2 is a diagram illustrating a schematic top view of an optical sensor arrangement for measuring an observable, according to some embodiments described in the disclosure.

In FIGS. 2 and 4 to 6, the same or corresponding features are designated using the same reference signs. In some embodiments, the sensor arrangement of FIG. 2 differs from the sensor arrangement of FIG. 1 only in that the optical filter, i.e. first optical element 2, is a Fabry-Perot resonator instead of a ring resonator. Alternatively or in addition to this, the ring resonator of the sensor element could also be replaced by a Fabry-Perot resonator having an optical length varying depending on the observable. Furthermore, it is not necessary that the optical filter, i.e. the first optical element 2, is an optical resonator. Instead, the optical filter can be given by any other wavelength selective element showing an adequate transmittance, in particular by an AWG. As can be seen in FIG. 2, the active layer 4 covers the optical resonator completely.

Figure 3:
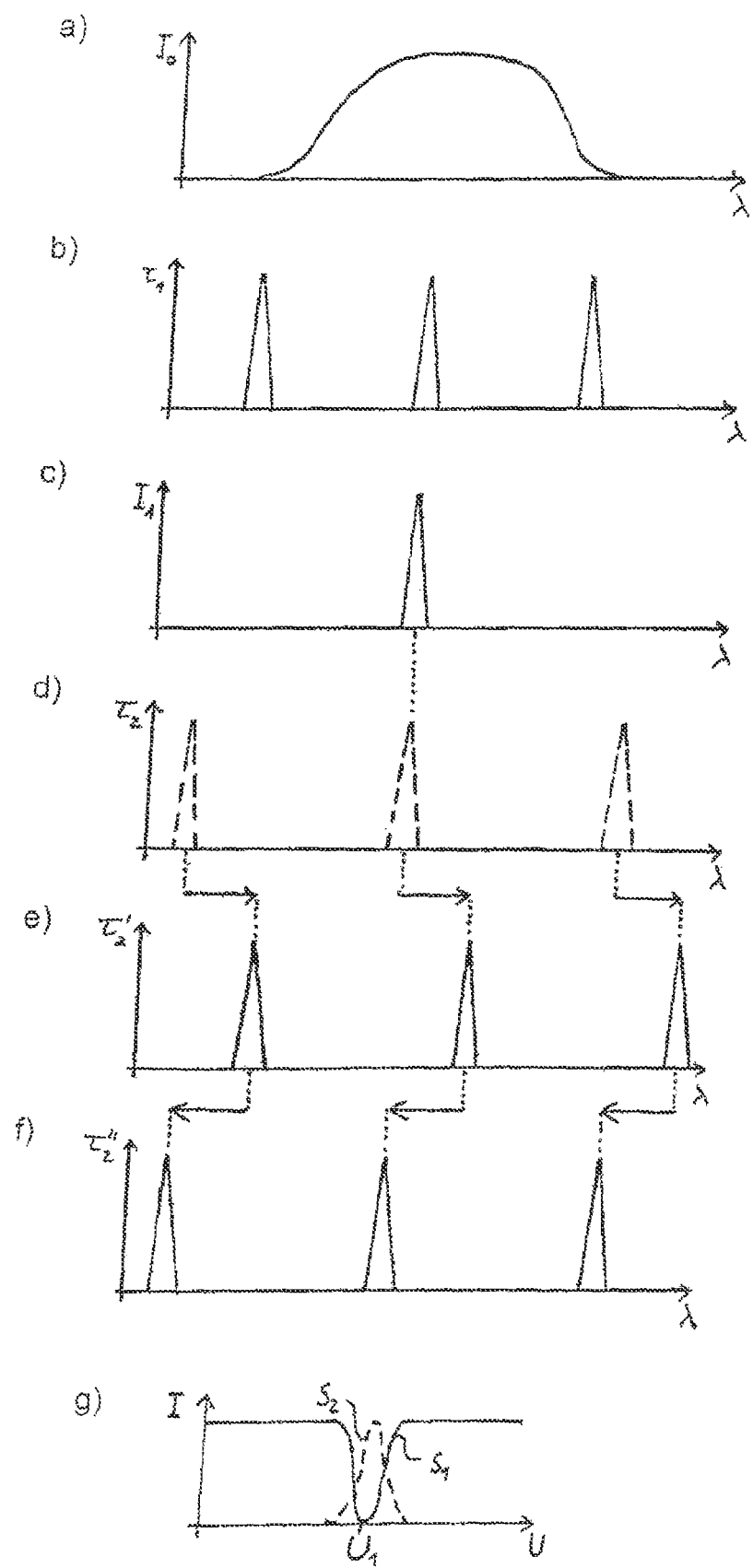
FIGS. 3a-3g are diagrams illustrating how the observable can be measured by means of any of these sensor arrangements, according to some embodiments described in the disclosure.

A method for measuring the observable by means of one of the optical sensor arrangements herein described is now explained with reference to FIG. 3. This figure shows in diagram a) the spectrum of the light which emitted by the light source 5 and fed via the first waveguide 8 into the optical filter. An intensity $I_0$ of this light is shown in this diagram as a function of the wavelength λ. A transmittance $\tau_1$ of the optical filter is shown in diagram b). This transmittance shows a plurality of peaks which are separated by a free spectral range. The size of this free spectral range will depend on the optical length of the respective micro ring resonator and may be, e.g., roughly 2 nm. At wavelengths in between the peaks, the transmittance $\tau_1$ becomes zero. A part of the light is transmitted by the optical filter and coupled into the second waveguide 9. Diagram c) of FIG. 3 shows a spectrum of this part, more precisely an intensity $I_1$ of this part of the light as a function of the wavelength λ. It can be seen that, in this case, one of the peaks of the transmittance $\tau_1$ coincides with one of the wavelengths emitted by the light source 5. Thus, the spectrum of said part of the light shows one sharp peak as well. Please note that it does not need to be excluded that more than one peak coincides with the wavelengths contained in the spectrum of the light source 5.

Via the second waveguide 9, said part of the light is coupled into the sensor element. Diagram d) shows a transmittance $\tau_2$ of the sensor element in a state where the sensor element is not exposed to an influence of the observable yet or where the observable has a known reference value. The transmittance $\tau_2$ is, in principle, similar to the transmittance $\tau_1$ of the optical filter and shows a plurality of peaks separated by free spectral ranges which are a bit different from the free spectral range of the optical filter. The sensor element is designed and/or tuned in a way that, in this state, one of the peaks of the transmittance $\tau_2$ coincides with the peak of the transmittance $\tau_1$ which coincides with one of the wavelengths of the lights source 5.

Thus, this peak of the transmittance $\tau_2$ and the peak of the spectrum shown in diagram c) coincide.

The first detector, which is situated at an end of the second waveguide 9, will detect a first component of said part of the light which is not transmitted by the sensor element. A second component of said part of the light which is transmitted by the sensor element is coupled into the third waveguide 10 and detected by means of the second photo detector 7. The reference configuration characterized by the transmittance $\tau_2$ shown in diagram d) can easily be found by tuning the sensor element such that at least almost 100% of the intensity $I_1$ a coupled into the third waveguide 10. In this state, the first photo detector 6 will detect a minimum while the second photo detector 7 detects a maximum.

Now, the sensor element is exposed to the influence of the observable to be measured. Where this observable is the presence or the concentration of a particular substance or group of substances selectively collected by the active layer 4, the sensor element is, to this end, brought into contact with a fluid to be analysed. The optical length of the sensor element will change if this fluid contains the substance or one of the substances to be detected.

Depending on a value of the observable—e.g. depending on whether said fluid contains the substance which is selectively collected by the active layer 4—the peaks of the transmittance $\tau_2$ are shifted by an amount which is a measure for this value. The resulting shifted transmittance $\tau_2'$ of the sensor element is shown in diagram e) of FIG. 3. Now, the sensor element is tuned by applying, dependent on output signals of the two photo detectors 6 and 7, a control signal to the sensor element. This control signal is determined, by the control unit 12, such that the resonance wavelength of the optical resonator which coincided with the peak of the spectrum shown in diagram c) before exposing the sensor element to the influence of the observable is shifted until this resonance wavelength and this peak are made to coincide again. The resulting transmittance $\tau_2''$ is shown in diagram f) and corresponds to the transmittance $\tau_2$ shown in diagram d). A strength of the control signal needed for shifting the resonance wavelengths of the sensor element accordingly is more or less proportional to the shift caused by the observable and, thus, is a measure for the observable.

Diagram g) illustrates how the control signal $U_1$ which is applied for tuning the sensor element as described above is found by the control unit 12. Diagram g) shows an output signal $s_1$ of the first photo detector 6 and an output signal $s_2$ of the second photo detector 7 as functions of the control signal U. The control signal $U_1$ for compensating the shift caused by the actual value of the observable is chosen such that an intensity I of the second component has a maximum value and an intensity I of the first component has a minimum value as this indicates that said resonance wavelength of the optical resonator and the peak coincide. In some embodiments, the optical filter can be tuned similarly instead of the sensor element such that the resonance wavelength and the peak are made to coincide. In this case, the control signal is applied to the optical filter and the peaks of the transmittance $\tau_1$ are shifted instead of the resonance wavelengths of the sensor element.

Figure 4:
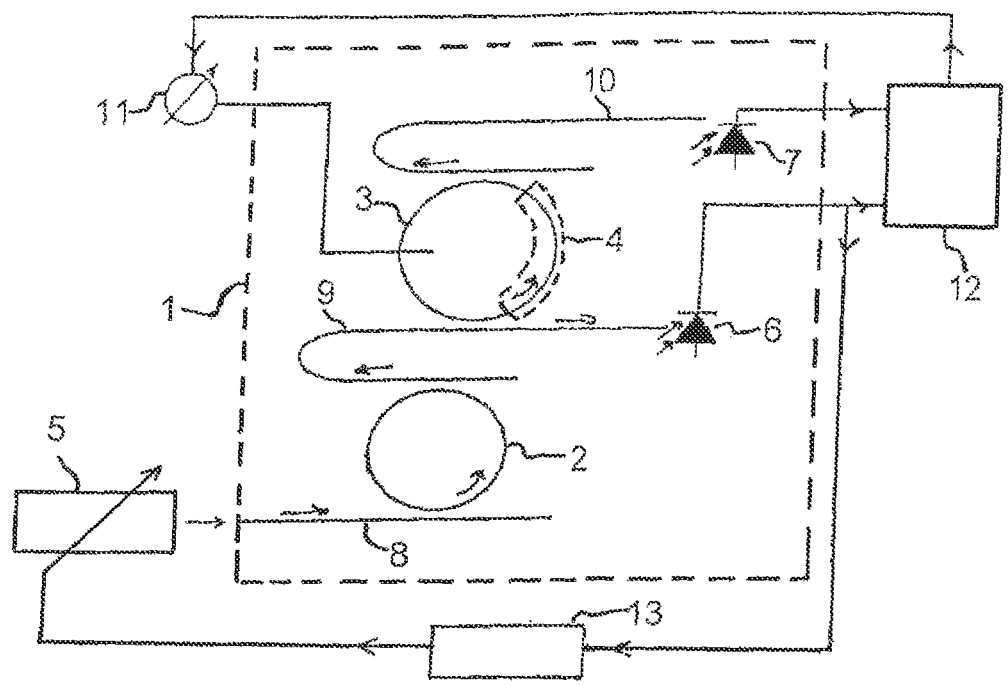
FIG. 4 is a diagram illustrating a schematic top view of an optical sensor arrangement for measuring an observable, according to some embodiments described in the disclosure.

The sensor arrangement shown in FIG. 4 is similar to the sensor arrangement of FIG. 1. The light source 5 is a tunable Fabry-Perot laser and the sensor arrangement features, in addition to what is described above, a feedback control system 13 for controlling the light source dependent on an output signal of the first photo detector 6. The Fabry-Perot laser has a multi mode spectrum and, therefore, would not be suitable for reading out a micro ring resonator without using an optical filter as described above. The output signal of the first photo detector 6 is used as a controlled variable of the feedback control system 13, which is configured for tuning the Fabry-Perot laser such that the relevant peak of the transmittance $\tau_1$ coincides with a peak of a spectrum of the Fabry-Perot laser. This can be done, for example, by temperature control of the light source 5. Assuming that the first optical element 2 and the second optical element 3 see the same environmental influences, this configuration eliminates the environmental influences and makes sure that the spectrum coupled out of the first optical element 2 is of the type shown in diagram c) of FIG. 3.

Figure 5:
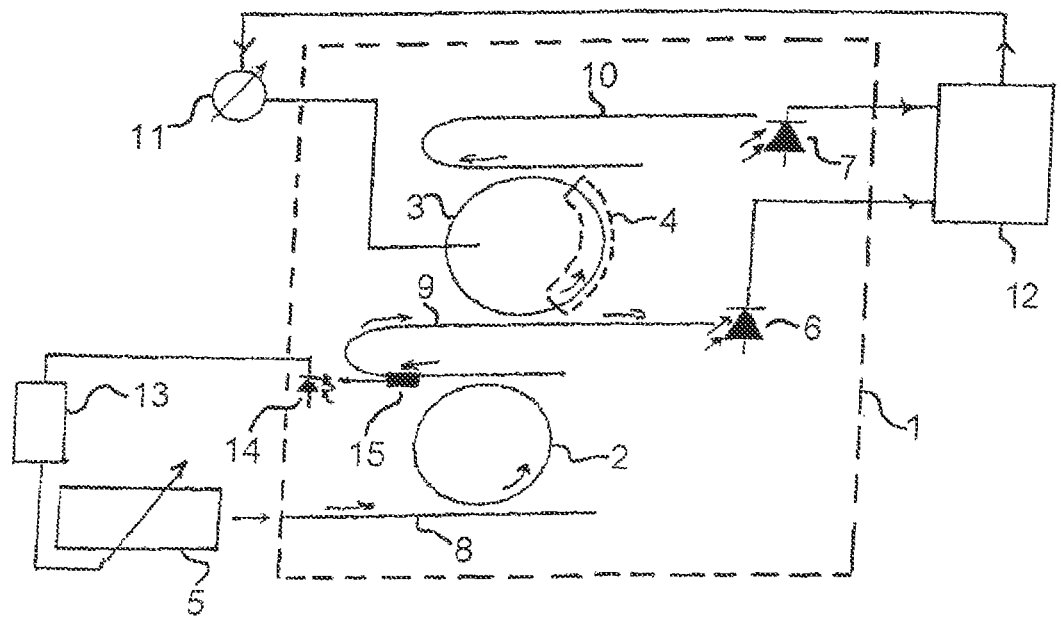
FIG. 5 is a diagram illustrating a schematic top view of an optical sensor arrangement for measuring an observable, according to some embodiments described in the disclosure.

FIG. 5 shows a sensor arrangement which differs from the sensor arrangement of FIG. 4 only in that a third photo diode 14 is used for generating the controlled variable of the feedback control system 13 instead of the first photo detector 6. To this end, a coupler 15 is provided for coupling out a small fraction of the part of the light led by the second waveguide 9.

Figure 6:
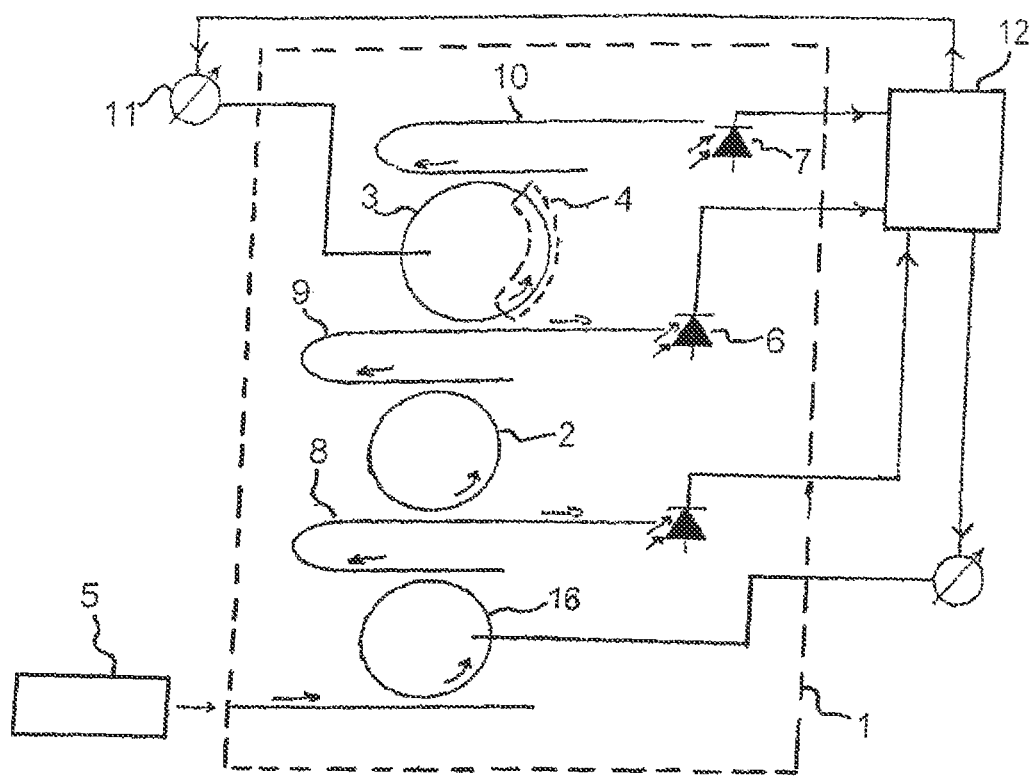
FIG. 6 is a diagram illustrating a schematic top view of an optical sensor arrangement for measuring an observable, according to some embodiments described in the disclosure.

Another sensor arrangement is shown in FIG. 6. This example shows that additional filters or resonators may be used for filtering the light produced by the light source 5. The sensor arrangement comprises a further micro ring resonator 16 for filtering the light of the light source 5 which may be a broad band light source. The micro ring resonator 16 is tuned by the control unit 12 such that a spectrum of the filtered light coupled into the waveguide 8 is suitable for feeding the sensor element, i.e. for feeding the second optical element 3, via the first optical element 2 in a way that the observable can be measured as described above.

The invention claimed is:

1. An optical sensor arrangement for measuring an observable, comprising:
    a light source for emitting light of a spectrum containing a plurality of different wavelengths;
    a first optical element;
    a second optical element;
    a first photo detector;
    a second photo detector; and
    a control unit,
        wherein the light source is optically coupled to the first optical element for feeding the light into the first optical element, the first optical element being optically coupled to the second optical element for feeding a part of the light transmitted by the first optical element into the second optical element,
        wherein the first photo detector is optically coupled to the first optical element for detecting a first component of said part of the light which is not transmitted by the second optical element, the second photo detector being optically coupled to the second optical element for detecting a second component of said part of the light which is transmitted by the second optical element,
        wherein one of the first and the second optical elements is an optical filter for filtering out a subset of said wavelengths, a transmittance of the filter showing at least one peak, the peak coinciding with one of said wavelengths, and
        wherein the remaining of the first and the second optical elements is a sensor element, the sensor element being an optical resonator, an optical length of this resonator being variable depending on the observable,
        the sensor element or the filter being tunable,
        wherein the control unit is configured for tuning the sensor element or the filter via a control signal, the control signal being adapted for shifting, dependent on output signals of the first and the second photo detectors, a resonance wavelength of the optical resonator or said peak such that the resonance wavelength and the peak are made to coincide, a strength of the shifting control signal being a measure for the observable.

2. The sensor arrangement of claim 1, wherein the optical filter is a further optical resonator or a wavelength selective element comprising an optical grating.

3. The sensor arrangement of claim 1, wherein at least one of the sensor element and the optical filter is a ring resonator or a Fabry-Perot resonator.

4. The sensor arrangement of claim 1, wherein the observable influencing the optical length of the sensor element is at least one of a temperature, a pressure, a mechanical stress, a humidity and a presence or concentration of a substance or of a group of substances to be detected.

5. The sensor arrangement of claim 4, wherein the sensor element is covered at least partially with an active layer of a covering material for selectively adsorbing the substance or the group of substances to be detected.

6. The sensor arrangement of claim 1, comprising a substrate, the substrate carrying the filter and the sensor element, at least one waveguide being arranged on the substrate for optically coupling the light source, the filter, the sensor element and the photo detectors.

7. The sensor arrangement of claim 1, wherein the light source is tunable and the sensor arrangement comprises a feedback control system for controlling the light source dependent on an output signal of the first or the second or a third photo detector, the feedback control system being configured for tuning the light source such that said peak is made to coincide with a maximum of the spectrum of the light emitted by the light source.

8. A method for measuring an observable by an optical sensor arrangement, the method comprising:
producing light by a light source, the light having a spectrum containing a plurality of different wavelengths;
feeding the light into a first optical element;
feeding a part of the light transmitted by the first optical element into a second optical element;
detecting, by at least two photo detectors, a first component and a second component of said part of the light, wherein the first component is not transmitted by the second optical element while the second component is transmitted by the second optical element,
wherein one of the first and the second optical elements is an optical filter for filtering out a subset of said wavelengths, a transmittance of the filter showing at least one peak, the peak coinciding with one of said wavelengths, and
wherein the remaining of the first and the second optical elements is a sensor element, the sensor element being an optical resonator, an optical length of this resonator being variable depending on the observable,
the method further comprising:
tuning the sensor element or the optical filter by applying, dependent on output signals of the photo detectors, a control signal to the sensor element or to the optical filter such that a resonance wavelength of the optical resonator or said peak is shifted until the resonance wavelength and the peak are made to coincide, a strength of the shifting control signal being a measure for the observable.

9. The method of claim 8, wherein the control signal applied for tuning the sensor element or the optical filter is chosen such that an intensity of the second component or of the first component has a maximum value and/or an intensity of the first component or of the second component has a minimum value, the maximum value and/or the minimum value indicating that said resonance wavelength of the optical resonator and the peak coincide.

10. The method of claim 8, wherein the optical filter is chosen to be a further optical resonator or a wavelength selective element comprising an optical grating.

11. The method of claim 8, wherein at least one of the sensor element and the optical filter is chosen to be a ring resonator or a Fabry-Perot resonator.

12. The method of claim 8, wherein the measured observable, which influences the optical length of the sensor element, is at least one of a temperature, a pressure, a mechanical stress, a humidity and a presence or concentration of a substance or of a group of substances to be detected.

13. The method of claim 12, wherein the sensor element is brought into contact with a fluid to be analysed, an active surface of the sensor element being configured such that the optical length of the sensor element changes when the fluid contains the substance to be detected.

14. The method of claim 8, wherein the light source is tuned using a feedback control system such that said peak is made to coincide with a maximum of the spectrum of the light emitted by the light source, an output signal of one of the two photo detectors or of a third photo detector being used as a controlled variable of the feedback control system.

* * * * *